United States Patent [19]

Tanaka

[11] 4,180,159
[45] Dec. 25, 1979

[54] MIXING TRAY ASSEMBLY

[76] Inventor: Asami Tanaka, 4840 Foster St., Skokie, Ill. 60077

[21] Appl. No.: 895,940

[22] Filed: Apr. 13, 1978

[51] Int. Cl.² .................. B65D 81/22; B67D 3/00; B44D 7/00
[52] U.S. Cl. .................. 206/63.5; 118/268; 206/1.7; 206/205; 222/187
[58] Field of Search .............. 206/63.5, 205, 210, 206/1.7, 1.8; 118/268; 222/187

[56] References Cited
U.S. PATENT DOCUMENTS

| | | | |
|---|---|---|---|
| 1,548,472 | 8/1925 | Lien | 118/268 |
| 2,554,302 | 5/1951 | Keskitalo | 118/268 |
| 2,827,012 | 3/1958 | Kesling | 118/268 |
| 3,786,913 | 1/1974 | Crawford | 206/1.8 |
| 3,885,843 | 5/1975 | Rubel | 206/1.7 |
| 3,966,094 | 6/1976 | Sheppard | 222/187 |

FOREIGN PATENT DOCUMENTS 6565 3/1907 United Kingdom .................. 206/1.8

*Primary Examiner*—William T. Dixson, Jr.
*Attorney, Agent, or Firm*—Neuman, Williams, Anderson & Olson

[57] ABSTRACT

A tray assembly is provided for use in mixing at least one ingredient with a liquid to form a product having a predetermined moisture content and then maintaining the said moisture content while the product is disposed within the tray assembly. The tray assembly includes a receptacle having a surface on which the product is mixed and supported thereby. Subtending in spaced relation the receptacle is a reservoir in which is disposed a predetermined amount of liquid. One end of an elongated wick is immersed within the liquid accumulated in the reservoir and the opposite end of the wick is disposed in the receptacle and in contact with the product therein.

7 Claims, 1 Drawing Figure

U.S. Patent
Dec. 25, 1979
4,180,159
FIG. 1
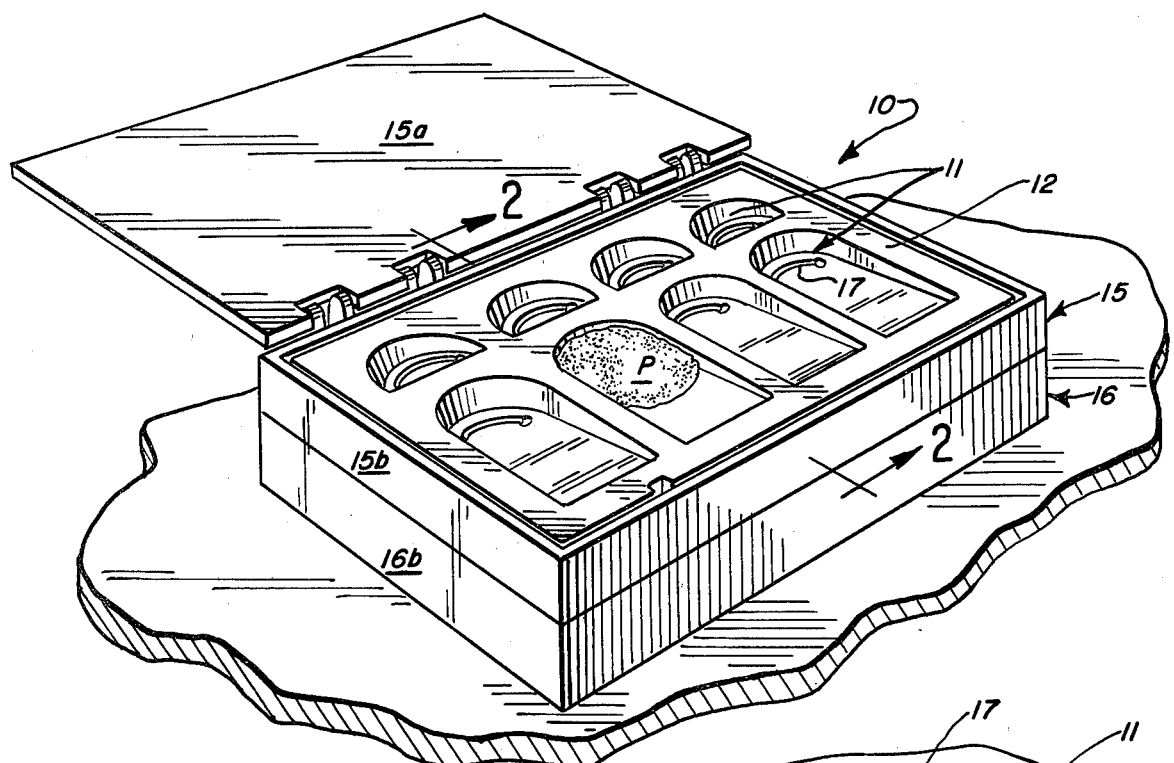
FIG. 2
FIG. 3
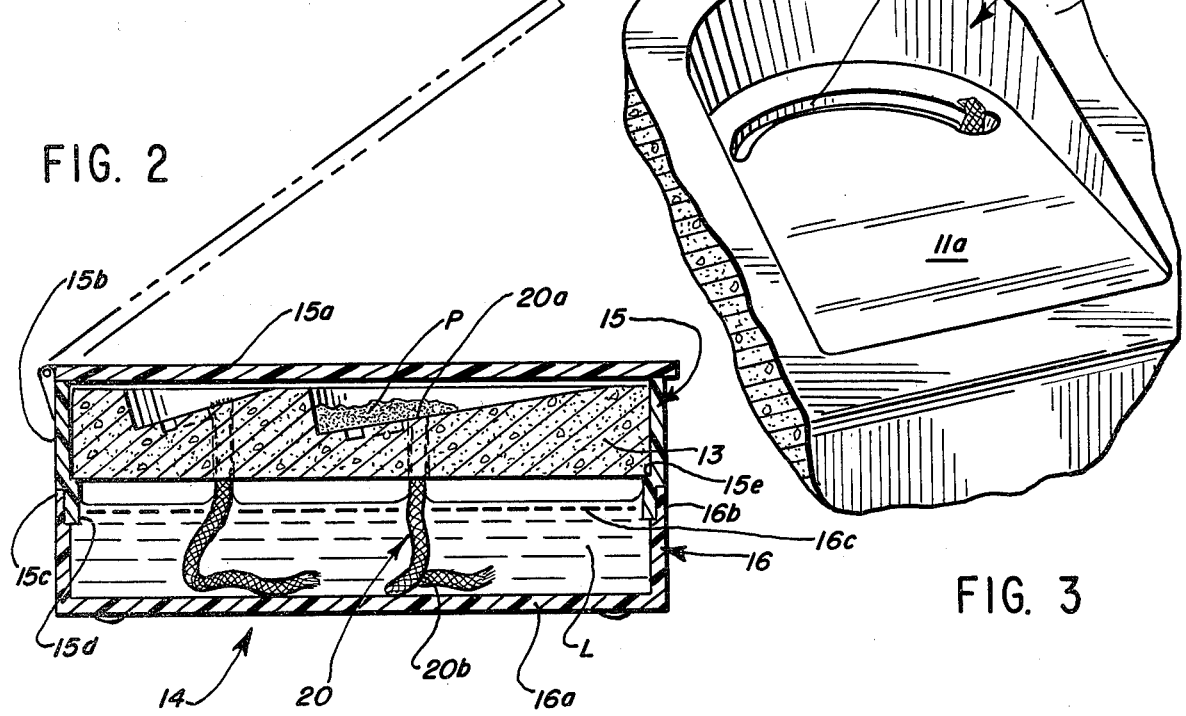

MIXING TRAY ASSEMBLY

BACKGROUND OF THE INVENTION

In the preparation of certain products such as, for example, porcelain used in dental restorative work, it is important that the moisture content of the product be properly controlled and maintained so as to avoid the problems of discoloration, deterioration and weakness. Heretofore, difficulty has been encountered in this regard because of the exposure to the atmosphere of the product for prolonged periods of time during the formation of the dental restorative and, thus, result in evaporation of the liquid from the product. Frequent and repeated manual replenishment of the evaporated liquid to the product was both awkward and inconvenient, involved guess-work on the amount of liquid to be replenished, and, thus, caused the consistency of the product to vary over a substantial range.

SUMMARY OF THE INVENTION

Thus, it is an object of the invention to provide a tray assembly of the type described which facilitates the mixing of the desired product and automatically maintains the proper moisture content of the product.

It is a further object of the invention to provide a tray assembly of the type described which enables a plurality of different products to be mixed on a given tray assembly and enables the various products to be segregated from one another while at the same time maintaining the moisture content of each product.

It is a still further object of the invention to provide a tray assembly of the type described which is of simple, yet sturdy construction; may be readily cleaned when required; and is capable of simultaneously accommodating a variety of products.

Further and additional objects will appear from the description, accompanying drawing and appended claims.

In accordance with one embodiment of the invention a tray assembly of the type described is provided which includes at least one receptacle having a surface on which an ingredient is mixed with a liquid to form a product having a predetermined moisture content. A portion of the receptacle surface is in supporting engagement with the product. Subtending in spaced relation the receptacle is a reservoir in which the liquid is accumulated. An elongated wick is provided having one end thereof immersed in the liquid accumulated in the reservoir. The opposite end of the wick extends through an opening formed in the surface portion of the receptacle and is in contact with the product supported by the surface portion whereby the wick will effect replenishment of the liquid in the product which has been removed therefrom by evaporation.

DESCRIPTION

For a more complete understanding of the invention reference should be made to the drawing wherein:

FIG. 1 is a perspective top view of one form of the improved tray assembly showing the cover thereof in a fully open position.

FIG. 2 is an enlarged sectional view taken along line 2—2 of FIG. 1 and showing the tray assembly with the cover thereof in a closed position; the cover in a partially open position is shown in phantom lines.

FIG. 3 is an enlarged fragmentary top perspective view of one of the receptacles shown in FIG. 1.

Referring now to the drawing and more particularly to FIG. 1, one form of the improved tray assembly 10 is shown which is suitable for use in mixing porcelain powder with various amounts of liquid (e.g., water) when a dentist or dental technician is making dental restoratives and the like. Preparatory to producing the dental restorative, a paste-like product P of porcelain powder and water is prepared and retained on the tray assembly in one of a plurality of receptacles 11 formed in exposed surface 12 of a plate member 13.

During the course of fabricating the dental restorative, which may be, for example, a full mouth denture, a pontic, or merely a crown affixed to an existing natural tooth, successive portions of the product are removed from the product disposed within the receptacle. Normally, the fabrication of the dental restorative involves a substantial period of time during which the product P within the receptacle is exposed to the atmosphere and the liquid within the product is subject to evaporation. It is an intent of the improved tray assembly 10 to automatically replenish the liquid within the product which is lost by evaporation and thereby maintain the desired consistency of the product during the dental restorative fabrication period.

The form of the improved tray assembly 10, shown in FIG. 1, includes a sectional housing 14 having an upper section 15 in which the plate member 13 is disposed and a lower section 16. As noted in FIG. 2, upper section 15 is adapted to be nested into lower section 16 when the housing is in an assembled condition.

The upper section 15, as seen more clearly in FIG. 2, includes a cover 15a which is hingedly connected along one edge to the side wall 15b of the section. The lower edge of the side wall 15b is provided with an exterior shoulder 15c which may be engaged by the upper edge 16a of section 16 when the sections 15, 16 are in assembled relation. In addition, the lower edge of side wall 15b delimits an open bottom 15d which communicates with the interior of the lower section 16. A ledge 15e is formed on the interior surface of side wall 15b and is adapted to supportingly engage the underside of plate member 13.

Lower section 16 includes a bottom panel 16a which is delimited by an upstanding side wall 16b. The upper edge of the side wall 16b defines an open top 16c into which the open bottom portion of the upper section 15 extends. A ledge 16d may be formed on the interior surface of side walls 16b against which the lower edge of the upper section 15 rests when the sections are in assembled relation. The lower section 16 serves as a reservoir for a liquid L (e.g., water). When section 15 is disassembled from section 16, the liquid may be readily poured into the section through the open top thereof. While the interior of section 16 is shown as a single reservoir the invention is not intended to be limited thereto. For example, if desired, the interior may be formed into a plurality of segregated reservoirs, each accommodating a different type of liquid. The sections 15, 16 may be formed of metal or a suitable plastic material.

Plate member 13 is preferably formed of a hard material which is inert to the product and is capable of withstanding repeated use and may be readily cleaned when required. As seen in FIG. 1, the upper exposed surface 12 of member 13 is provided with a plurality of receptacles 11 which are segregated from one another. The size, shape, number and arrangement of the receptacles may vary from that shown without departing from the scope of the invention. Each receptacle 11, one of which is shown in detail in FIG. 3, includes a bottom surface 11a which is inclined towards one end or edge thereof. The surface enables the product ingredients to be readily mixed thereon and then a mass of the resulting product is supported at the lower portion of the surface.

Formed within the lower surface portion is an elongated trough or recess 17 which extends across substantially the width of the surface 11a, see FIG. 3. Communicating at one end of the trough 17 is a depending opening 18 which terminates at the underside of member 13.

Positioned within each opening 18 is a wick 20 which has the upper end 20a thereof contacting the product P. The lower end portion 20b of the wick is immersed in the liquid L accumulated in the reservoir disposed therebeneath and formed in the interior of housing section 16. The wick 20 automatically maintains the desired moisture content of the product even though the latter is exposed to the atmosphere for prolonged periods of time. The wick will also maintain a level of liquid within the trough 17 and because of the length of the latter, a substantial part of the supported product mass will be in contact with the liquid.

By having several segregated receptacles 11 and/or liquid reservoirs, numerous products of differing formulations may be supported at one time on the plate member 13 to meet the requirements of various types of dental restoratives. When none of the products is being used the cover 15a of section 15 may be adjusted to a closed position whereby continued evaporation of the liquid from any product remaining in a receptacle 11 will be markedly retarded.

Thus, with the improved tray assembly, continued monitoring by the dentist or technician of the product or products disposed within the receptacles is not required so that the moisture content of each product remains stable, even though the cover 15a assumes an open position for a substantial period of time. The dentist or technician, therefore, may devote his or her attention to other aspects involved in fabricating a dental restorative. The tray assembly is of compact, simple, sturdy, and inexpensive design and is capable of simultaneously accommodating a variety of products.

I claim:

1. A tray assembly for use in mixing at least one ingredient with a liquid to form a product having a predetermined moisture content and maintaining the moisture content thereof while the product is disposed within the tray assembly; said tray assembly comprising a receptacle having a surface for mixing and supporting thereon the product and an elongated trough in said surface for delivering the liquid to a substantial part of the supported product, a reservoir for the liquid mounted in spaced subtending relation with respect to said receptacle, and an elongated wick having one end thereof disposed within said reservoir and adapted to be immersed within the liquid accommodated therein and a second end thereof disposed within said receptacle and communicating with said trough and the portion of said surface adjacent thereto whereby the moisture content of the product is replenished by capillary action of the liquid from the reservoir through the wick to the trough and product.

2. The tray assembly of claim 1 wherein the surface of said receptacle is inclined towards one side thereof and the surface portion of the receptacle contacted by the second end of the wick and the trough is adjacent said one side.

3. The tray assembly of claim 2 wherein the surface portion of the receptacle adjacent said one side thereof is provided with an opening through which the wick extends; said opening being in communication with the trough.

4. A tray assembly of claim 1 wherein said receptacle and reservoir are enclosed within a housing having separable upper and lower complemental sections; the upper section including the receptacle and the lower section including the reservoir.

5. The tray assembly of claim 4 wherein the housing sections, when assembled, are arranged in nested relation, and said upper section is provided with an open bottom in communication with an open top provided in said lower section.

6. The tray assembly of claim 1 including a plurality of receptacles arranged in relatively spaced relation, and a plurality of elongated wicks, one for each receptacle.

7. The tray assembly of claim 6 wherein each receptacle has a mixing and product supporting surface inclined towards one side thereof and the surface portion of each receptacle contacted by the second end of the wick is adjacent said one side and is provided with a wick opening and an elongated trough in communication therewith.

* * * * *